US005789414A

United States Patent [19]

Lapidot et al.

[11] Patent Number: 5,789,414
[45] Date of Patent: Aug. 4, 1998

[54] PHARMACEUTICAL COMPOSITIONS COMPRISING TETRAHYDROPYRIMIDINE DERIVATES

[75] Inventors: Aviva Lapidot; Livia Inbar, both of Rehovot; Edna Ben-Asher, Tel Aviv; Yosef Aloni, deceased, late of Rehovot, all of Israel, by Chayuta Aloni, Legal Representative

[73] Assignee: Yeda Research and Development Co. Ltd., Rehovot, Israel

[21] Appl. No.: 11,668

[22] Filed: Jan. 28, 1993

[30] Foreign Application Priority Data

Jan. 30, 1992 [IL] Israel .................................. 100810

[51] Int. Cl.$^6$ .............................................. A61K 31/505
[52] U.S. Cl. ............................... 514/256; 514/269
[58] Field of Search ........................ 544/298, 335; 514/269, 256

[56] References Cited

U.S. PATENT DOCUMENTS 4,261,995  4/1981  Weinhardt et al. .................. 544/330

OTHER PUBLICATIONS

Inbar et al. J. Bacteriol. 170, 4055 (1988).
Inbar et al. J. Biol. Chem. 263, 16014–16022 (1988).
Inbar et al. J. Bacteriol. 173 7790 (1991).
Okuda et al. Chem. Abstracts, vol. 113–129062 (1990).
Livia Inbar and Aviva Lapidot, "Metabolic Regulation in Streptomyces parvulus during Actinomycin D Synthesis, Studied with $^{13}$C–and $^{15}$N–Labeled Precursors by $^{13}$C and $^{15}$N Nuclear Magnetic Resonance Spectroscopy and by Gas Chromatography–Mass Spectrometry", Journal of Bacteriology, Sep. 1988, pp. 4055–4064, Copyright 1988, American Society for Microbiology, vol. 170. No. 9.
Petra Peters, E.A. Galinski and H.G. Truper, "The biosynthesis of ectoine", FEMS Microbiology Letters 71 (1990) 157–162, Published by Elsevier, pp. 157–162.
Galinsky, et al., "1,4,5, 6–Tetrahydro–2–methyl–4–pyrimidinecarboxylic acid A novel cyclic amino acid from halophilic phototrophic bacteria of the genus Ectothiorhodospira", pp. 135–139. (no year) Journal? vol. ?.
Erwin A. Galinski and Karin Lippert, "Novel Compatible Solutes And Their Potential Application As Stabilizers In Enzyme Technology", General and Applied Aspects of Halophilic Microorganisms, New York 1991, pp. 351–358.
Ronit Regev, et al., "C NMR Study of the Interrelation between Synthesis and Uptake of Compatible Solutes in Two Moderately Halophilic Eubacteria", Archives of Biochemistry and Biophysics, vol. 278, No. 1, Apr., pp. 106–112. no year.

Stephen C. Brown, ET AL., "Aqueous Solution Structure of an Intercalated Actinomycin D–dATGCAT Complex by Two–Dimensional and One–Dimensional Proton NMR", Biochemistry 1984, pp. 403–408.
Erwin A. Galinski, ET AL., "The Crystal Structure of Extoine, a Novel Amino Acid of Potential Osmoregulatory Function", pp. 780–784, vol. 3 no year, Journal?.
Axel Wohlfarth, ET AL., "The spectrum of compatible solutes in heterotrophic halophilic eubacteria of the family Halomonadaceae", Journal of General Microbiology (1990), pp. 705–712, printed in Great Britain.
Terry P. Lybrand, ET AL., "Computer Modeling of Actinomycin D Interactions with Double–helical DNA", J. Mol. Biol. (1986) 191, pp. 495–507.
Ning Zhou, ET AL., "Binding of Actinomycin D to |d(ATC-GAT)| 2: NMR Evidence of Multiple Complexes", Biochemistry 1989, 28, pp. 5231–5239.
V.V. Nosikov, et al., "Protection of particular cleavage sites of restriction endonucleases by distamycin A and actinomycin D", Nuclear Acids Research, vol. 3, No. 9, Sep. 1976, pp. 2293–2301.
L. Inbar and A. Lapidot, "$^{13}$ C Nuclear Magnetic Resonance and Gas Chromatography–Mass Spectrometry Studies of Carbon Metabolism in the Actinomycin D Producer Streptomyces parvulus by Use of $^{13}$C–Labeled Precursors", Journal of Bacteriology, Dec. 1991, pp. 7790–7801.
Henry G. Hodo III and Stanley P. Blatti, "Purification Using Polyethylenimine precipitation and Low Molecular Weight Subunit Analyses of Calf Thymus and Wheat Germ DNA–Dependent RNA Polymerase II" pp. 2334–2343, Biochemistry, vol. 16, No. 11, 1977.
Livia Inbar and Aviva Lapidot, "The Structure and Biosynthesis of New Tetrahydropyrimidine Derivatives in Actinomycin D Producer Streptomyces parvulus", pp. 16014–16022, The Journal of Biological Chemistry, vol. 263, No. 31 Issue of Nov. 5, 1988.
Patent Abstracts of Japan, unexamined applications, C field, vol. 14, No. 310, Jul. 4, 1990. The Patent Office Japanese Government, p. 40 c 736, No. 2–104 577 (Koei Chem).

*Primary Examiner*—John M. Ford
*Attorney, Agent, or Firm*—Helfgott & Karas, P.C.

[57] ABSTRACT

A pharmaceutical composition comprising as active ingredients at least two tetrahydropyrimidine derivatives selected from (a) 2-methyl-4-carboxy-3,4,5,6-tetrahydropyrimidine [THP(B)] or a salt thereof, and (b) 2-methyl-4-carboxy-5-hydroxy-3,4,5,6-tetrahydropyrimidine [THP(A)], or a salt, a 5-ether or a 5-ester thereof, and a pharmaceutically acceptable carrier.

5 Claims, 11 Drawing Sheets

| adriam ug/ml | %3H dT | %3H dT + THPs |
|---|---|---|
| 1 | 0.000 | 100.000 | 100.000 |
| 2 | 0.010 | 72.000 | 107.000 |
| 3 | 0.020 | 60.000 | 93.000 |
| 4 | 0.050 | 65.000 | 68.000 |

PHARMACEUTICAL COMPOSITIONS COMPRISING TETRAHYDROPYRIMIDINE DERIVATES

The present invention relates to purified tetrahydropyrimidine derivatives and to pharmaceutical compositions comprising them. More particularly, the invention relates to tetrahydropyrimidine derivatives useful for DNA protection from damaging by DNA-binding drugs, chemical carcinogens and mutagens and from irradiation.

Actinomycins, a class of antitumor antibiotics used in cancer chemotherapy, prevent cell replication by positioning themselves between planar base pairs of DNA, thus preventing the unwinding of the double helix, and also inhibit transcription, i.e., DNA-dependent RNA synthesis, both in vivo and in vitro. The transcriptional inhibition in vivo or in vitro is thought to occur through binding of the drug to DNA and blockage of the RNA polymerase during elongation. Intercalators of DNA, such as actinomycin D and daunomycin, were shown to affect the DNA secondary structure.

Actinomycin D (hereinafter Act D), also called dactinomycin, and adriamycin are well known antitumor antibiotics. However, their high toxicity prevents their general use in cancer chemotherapy. It would be highly desirable to lower the toxicity of Act D and of other antitumor and cytotoxic antibiotics, thus allowing their effective use in antitumor therapy.

Two previously unknown metabolites tetrahydropyrimidine derivatives, 2-methyl-4-carboxy-5-hydroxy-3,4,5,6-tetrahydropyrimidine (designated THP(A) hereinafter) and 2-methyl-4-carboxy-3,4,5,6-tetrahydropyrimidine (designated THP(B) hereinafter), were found by the inventors of the present patent application to accumulate intracellularly in Act D-producing gram-positive actinomycete, *Streptomyces parvulus*, and were identified by in vivo and in vitro NMR studies, but were neither isolated nor purified (Inbar and Lapidot, 1988a, 1988b, 1991).

THP(B) in purified form had earlier been extracted from the culture of *Ectothiorhodospira halochloris*, an extremely halophilic bacteria. It was called "ectoine" and suggested to serve an osmoregulatory function (Galinski et al., 1985). Crystals of THP(B).CH$_3$OH were crystallized from water-free methanol (Schuh et al., 1985). Ectoine, a cyclic amino acid, was later found in a variety of different halophilic and halotolerant eubacteria, which are organisms of extremely saline habitats, such as *Halomonas elongata, Deleya halophila, Halomonas halmophila, Bacterium Ba$_1$, Vibrio costicola* and *Brevibacterium linens*. The natural environment of these microorganisms—salt or soda lakes, solar salterns, coastal lagoons or sea water, is characterized by a high ionic concentration and low water activity. For the maintenance of osmotic equilibrium, most halophilic eubacteria as well as yeasts, algae and fungi, accumulate inorganic ions, such as K$^+$, Na$^+$ and Cl$^-$, and neutral non-ionic organic molecules of low molecular weight, represented by the following major classes: polyols, sugars, some amino acids, betaines and ectoines. These solutes are called "compatible solutes" because they compensate the osmotic pressure and, by definition, are compatible with the metabolism of the cell. Apart from their purely osmotic function, compatible solutes, including ectoine, also exhibit protective effect on enzymes, e.g. against heating, freezing and drying (Wohlfarth et al., 1990; Regev et al., 1990; Peters et al., 1990; Galinski and Lippert, 1991). Japanese Patent Application published under No. 3031265, of Takeda Chemical Ind., discloses the chemical synthesis of ectoine and adds that it is useful as intermediate for medical agent, agricultural agent or organic electronic materials. None of the prior art discloses any pharmaceutical effect of THP(A) and THP(B), and particularly not their effect in protecting DNA from damage.

The inventors propose that there is a similarity in self-defence strategies in Act D-producing bacteria and halophilic eubacteria. The question of how antibiotic-producing organisms avoid suicide has been the subject of many studies. The target for drug action is known to be refractory to the endogenous antibiotics in the various organisms that produce them, although in many cases, the basis of such resistance has not been fully established. Only a few mechanisms of self-modification of antibiotic target sites have been characterized. In cases in which the antibiotic is involved in protein synthesis, self-protection depends on specific methylation of the ribosomal RNA target. However, interference with the antibiotic's ability to bind at the DNA target has not yet been achieved.

Act D is a potent inhibitor of DNA-dependent RNA synthesis. Since *S. parvulus* produces Act D during the normal course of its development, synthesizing RNA while simultaneously producing the antibiotic, it seems possible that resistance of the transcriptional machinery to Act D might be a characteristic of the cells.

Similarly, the resistance of the transcriptional machinery in halophilic microorganisms to high electrolyte concentrations might be an intrinsic feature of these cells. Since DNA at physiological pH is a very highly charged polyanion and so is surrounded by cations, the binding of proteins to DNA results in their displacement from the surface area of the DNA. How DNA-protein interactions are buffered in vivo in halophilic bacteria against the adverse effects of fluctuations in cellular ion concentration is a challenging question in the field of osmoregulation. The halophilic organisms must adopt survival strategies in order to avoid structural disturbances of cellular macromolecules at high intracellular potassium ion concentrations. Various antibiotic-producing strains of the Streptomyces genus were isolated from soil after being exposed to localized changes in soil salinity. It is herein proposed that similar mechanisms exist in these microorganisms to regulate responses both to antibiotic and osmotic stress.

Intracellular effectors were observed using NMR techniques to elucidate the mechanisms of self-defense in antibiotic-producing organisms. In the study of the control mechanism of Act D biosynthesis by *S. parvulus*, THP(A) and THP(B) were identified and found to accumulate intracellularly (Inbar and Lapidot, 1988a). Labeling experiments established that the THPs are not precursors of Act D (Inbar and Lapidot, 1988b). By NMR and X-ray crystallography of isolated and purified THP(A) and THP(B) according to the invention, it is shown here that the THPs form zwitterionic molecules with the half-chair conformation (FIG. 1).

According to the present invention, it was found that THP(A) and THP(B) are present not only in *S. parvulus*, but also in closely related Act D-producing microorganisms, such as *Streptomyces chrysomallus* and *Streptomyces antibioticus*, as shown by $^{13}$C NMR experiments according to the invention that revealed clearly that THP(A) and THP(B) were produced in these strains during Act D synthesis. The finding of THPs in several streptomycetes producing Act D, their relatively high intracellular concentrations during Act D synthesis, and the identity of the time of onset of their synthesis with that of Act D synthesis, indicate that they may function in the self-defense mechanism of Act D-producing organisms. Furthermore, using an in vitro transcription system (Kadesch and Chamberlin, 1982) in which RNA polymerase II was completely inhibited by Act D, THP(A) and THP(B) were found to act in concert to partially restore RNA polymerase activity.

It was thus found, in accordance with the present invention, that THP(A) alone or THP(A) and THP(B) in combination can protect DNA from digestion by restriction endonucleases. They also enable efficient growth of *E. coli* under high salt concentrations or in the presence of adriamycin, conditions which otherwise prevent *E. coli* growth. Furthermore, THP(A) and THP(B) function synergistically to prevent DNA—Act D complex formation. THP(A) alone or a mixture of THP(A) and THP(B) further have a direct effect on RNA transcription in the presence of Act D, as demonstrated in an in vitro transcription assay.

It is an object of the present invention to provide pharmaceutical compositions comprising THP(A) and/or THP (B), and a pharmaceutically acceptable carrier. These compositions will particularly protect DNA in non-tumor tissues from damaging by DNA-binding drugs, such as toxic antitumor drugs, or by chemical carcinogens and mutagens or irradiation, such as UV irradiation.

The pharmaceutical compositions of the invention comprise as active ingredient a tetrahydropyrimidine derivative selected from 2-methyl-4-carboxy-5-hydroxy-3,4,5,6-tetrahydropyrimidine (THP(A)), a salt, a 5-ether or a 5-ester thereof, and/or 2-methyl-4-carboxy-3,4,5,6-tetrahydropyrimidine (THP(B)) or a salt thereof, and a pharmaceutically acceptable carrier.

It is a further object of the invention to provide THP(A) in substantially pure and in crystalline form as well as crystalline THP(B).2H$_2$O. It has been found that the conformation of THP(A) and THP(B) in the solid state is identical to their respective conformation in solution.

A further object of the invention is to provide for methods of obtaining THP(A) and THP(B) in substantially pure form. THP(A) and THP(B) may exist as racemates or in optically active forms. The natural products purified according to the invention were found to have the S form and to be biologically active.

Other objects and advantages of the invention will become apparent from the disclosure of the invention.

THP(A) and THP(B) can be obtained synthetically or can be isolated and separated in purified form from natural sources, such as cell extracts of Act D-producing microorganisms of the Streptomyces species, e.g. *S. parvulus*, *S. chrysomallus*, or *S. antibioticus* and mutants thereof. THP (B) alone can be isolated and purified from halophilic and halotolerant bacteria under salt stress, such as bacteria of the genus Ectothiorhodospira, e.g. *E. halochloris*, *E. halophila* and mutants thereof, or from heterotrophic halophilic eubacteria of the family Halomonadaceae. THP(A) alone can be produced by soil microorganisms of the Streptomyces species, e.g., *S. clavuligerus*, *S. griseus* and mutants thereof, under low salt stress.

In accordance with one preferred embodiment of the invention, THP(A) and THP(B) are isolated and purified from cell extracts of an Act D-producing Streptomyces strain by a method comprising the following steps:

(a) cultivating said Streptomyces strain in a suitable growth medium;

(b) harvesting the cells and preparing cell extracts from the washed cells;

(c) separating the tetrahydropyrimidine derivatives THP(A) and THP(B) from accompanying carbohydrates, polyols, amino acids, peptides and proteins by several column chromatography separation steps;

(d) subjecting the solution containing the two tetrahydropyrimidine derivatives to ion exchange column chromatography; and (e) eluting each tetrahydropyrimidine derivative with a different eluent, whereby substantially pure THP(A) and THP(B) are obtained.

The Act D-producing Streptomyces strain preferably used in the invention is *S. parvulus*, more particularly *S. parvulus* ATCC 12434, freely available from ATCC.

Cell extracts are prepared by methods known in the art, e.g. by suspending washed cell pellets in water and heating at 100° C. or by perchloric acid procedure. The cell extracts are then first mixed with acetic acid before subjecting them to separation procedures. First, carbohydrates and polyols are removed, e.g., by water; then amino acids are removed by anion exchange chromatography, and residues of intracellular peptides and proteins are removed by Sephadex G25. The separation of THP(B) from THP(A) in step (d) is then carried out on a Dowex 50W (NH$_4^+$ form) column and in step (e), THP(A) is eluted with water and THP(B) with 3M ammonium hydroxide.

In another preferred embodiment, THP(A) is isolated and purified from cell extracts of a Streptomyces strain isolated from soil by a method similar to that described above and which comprises the following steps:

(a) cultivating said Streptomyces strain in a suitable growth medium in 0.25M–0.5M NaCl;

(b) harvesting the cells and preparing cell extracts from the washed cells;

(c) separating THP(A) from accompanying carbohydrates, amino acids and proteins by several column chromatography separation steps;

(d) subjecting the solution containing THP(A) to ion exchange column chromatography; and (e) eluting the THP(A) with water, whereby substantially pure THP(A) is obtained.

The soil Streptomyces strains preferably used in the invention are *S. clavuligerus*, more particularly *S. clavuligerus* NRRL 3585, freely available from NRRL, and *S. griseus*, particularly *S. griseus* ATCC 10137, freely available from ATCC.

The salts of THP(A) and THP(B) to be used in the pharmaceutical compositions of the invention are physiologically acceptable salts, formed both with inorganic and organic bases. The 5-ethers of THP(A) include lower alkyl ethers and ethers formed with sugar moieties, e.g., nucleoside analogues, and are prepared by reaction with the suitable alcohols by methods known in the art. The 5-esters of THP(A) include lower alkanoyl esters prepared by reaction with suitable lower alkanoic acids.

THP(A) or THP(B) or the combination thereof may be used for protecting DNA in non-tumor tissues from damage by a DNA-binding drug in patients undergoing treatment with the DNA-binding drug. The DNA-binding drug may be any of the antitumor antibiotics presently used in cancer chemotherapy, e.g. dactinomycin (Act D), daunorubicin, doxorubicin (adriamycin), bleomycin, mitomycin and the like. Since these antitumor antibiotics are toxic to normal tissue, THP(A) or THP(B) or the combination of THP(A) and THP(B) will decrease their toxic effects. Other antitumor antibiotics not currently used in cancer chemotherapy due to their high toxicity, such as the anthracycline antibiotics cinerubins A and B, might have their toxicity reduced by THP(A), THP(B) or by THP(A)+THP(B), thus allowing their future use in antitumor therapy.

THP(A), THP(B) or the combination thereof may also be useful for protection of DNA from chemical carcinogens and mutagens, including irradiation.

THP(A) and THP(B) are not toxic to mammals. When administered to mice in doses of 1, 10 and 100 mg/100 g body weight, no toxic effects were found. THP(A) and THP(B) also do not have antibiotic activity, as shown in tests carried out on several cultures of gram positive and gram negative bacteria.

THP(A) or a salt, a 5-ether or a 5-ester thereof, and THP(B) or a salt thereof are formulated into pharmaceutical compositions by mixing therapeutically effective amounts of said compounds with a pharmaceutically active carrier. Additives, such as stabilizers, etc., can be added to the composition.

Pharmaceutical compositions for any suitable mode of administration are included in the invention, but preferred are single dose intravenous injections and intravenous infusions.

The molar ratio between THP(A) and THP(B) in the pharmaceutical compositions of the invention comprising both may vary. Preferably, the pharmaceutical compositions of the invention will comprise THP(A) and THP(B) in equimolar amounts.

The effective amounts of THP(A) and THP(B) alone or in combination in the compositions of the invention will vary according to the patient's condition, the severity of the disease and the amount of antitumor drug administered to him. In one embodiment, they will be administered in excess amount to the antitumor drug.

The pharmaceutical compositions of the invention may be administered prior to, together with, or preferably subsequently to, the administration of the antitumor antibiotic. In effective amounts they will decrease the toxic effects of the antitumor drug.

The invention is illustrated by way of example only, with reference to the accompanying drawings in which.

Figure 3C:
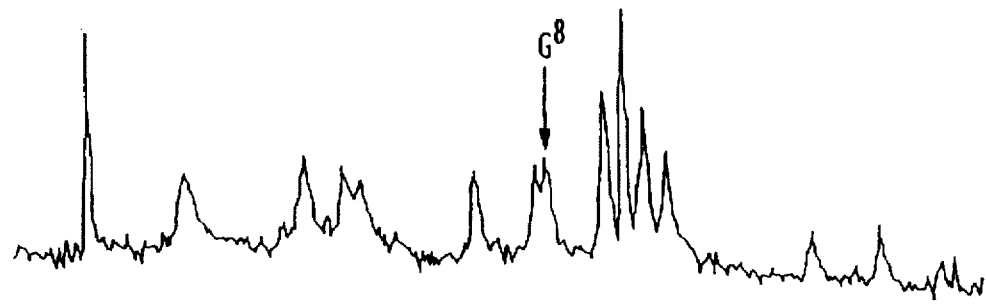
Figure 3B:
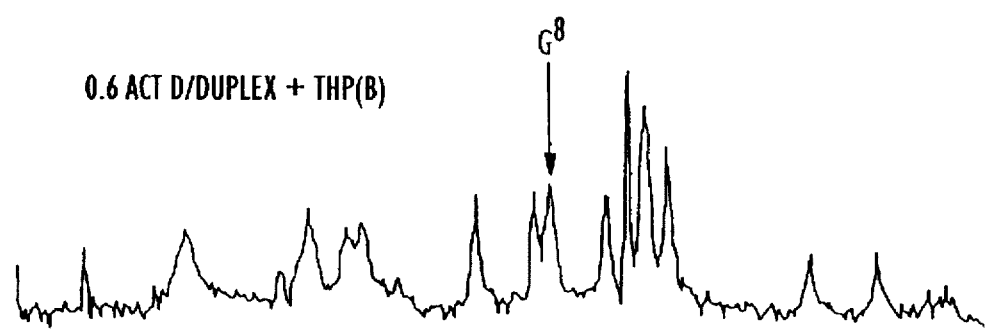
Figure 3A:
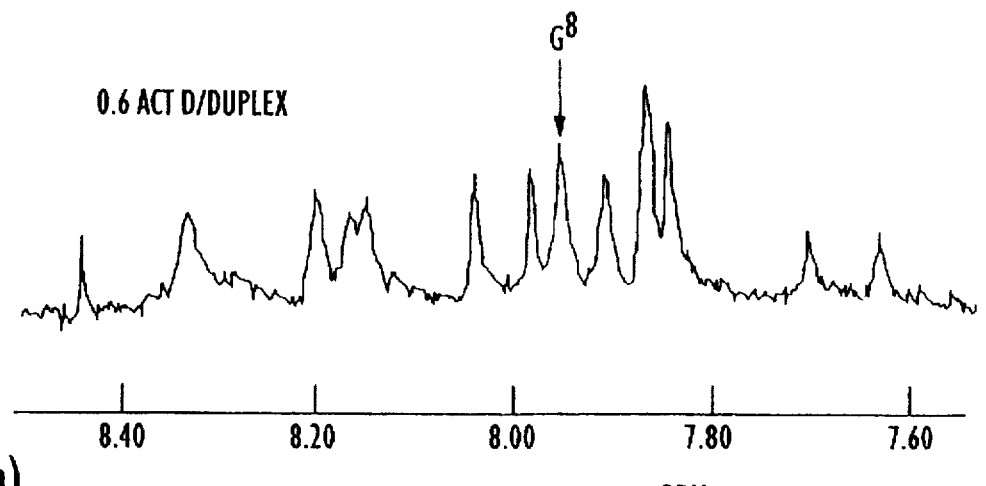

FIG. 3 shows the proton NMR spectra (7.6–8.4 ppm; 500 Mhz) of: (a) an Act D-d(ATGCAT) mixture at a ratio of 0.6:1; (b) after addition of THP(B) to the mixture at a ratio of 0.6:1:30, and (c) after addition of THP(A) to the mixture in (b) at a ratio of 0.6:1:30:30. Spectra were obtained in $D_2O$ phosphate buffer solution, pH 7 at 10° C. using solvent suppression by irradiation during acquisition delay. These experiments were done using a 4.0 mM stock solution of Act D and a 100 mM stock solutions of THP(A) and THP(B) in phosphate buffer. For each $^1$H NMR experiment 1.8 mg d(ATGCAT) in 0.45 ml phosphate buffer was used.

Figure 4B:
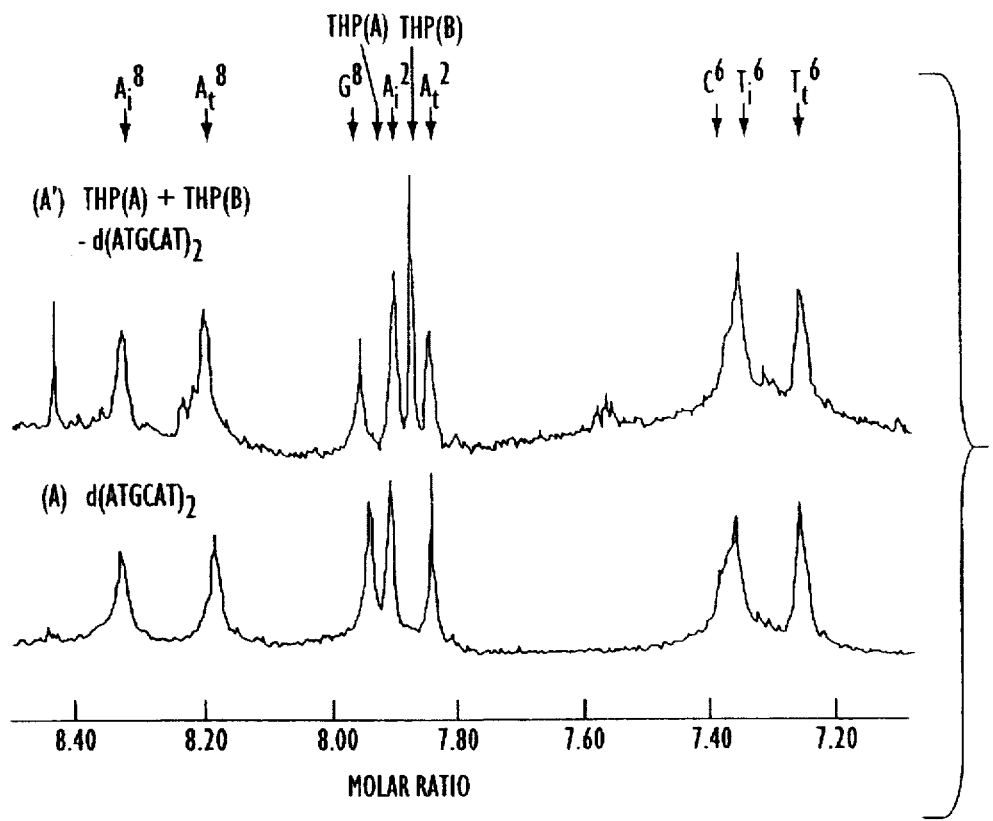
Figure 4A:
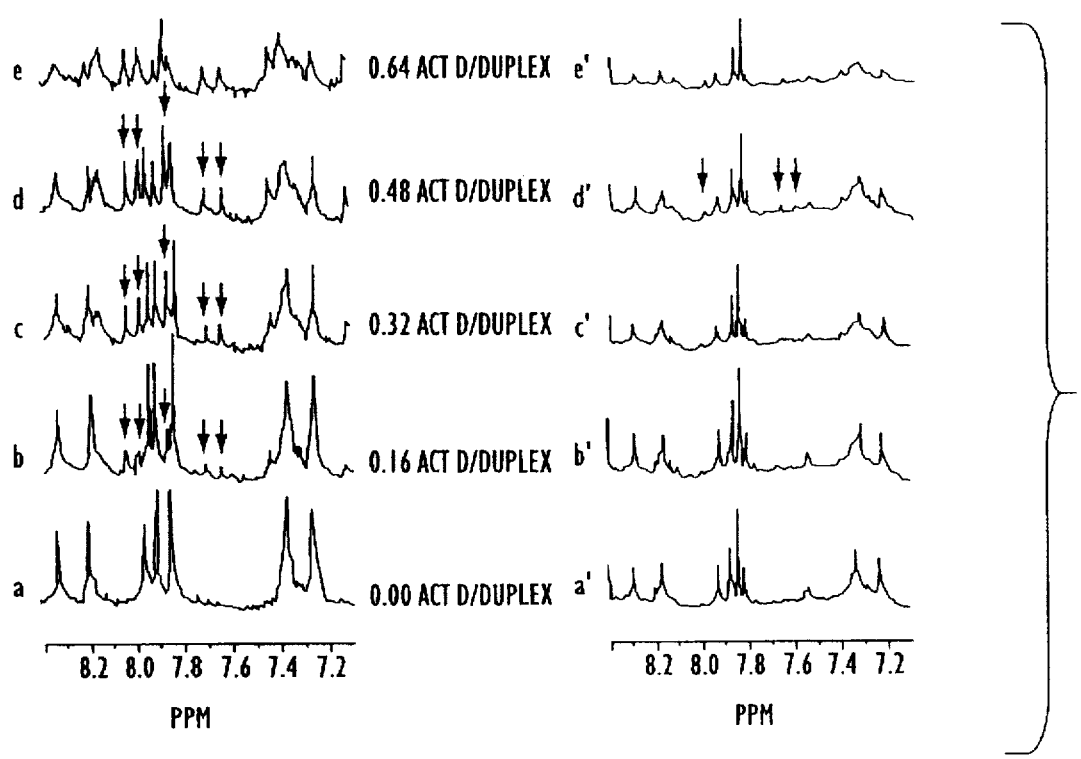

FIG. 4(a) shows the base aromatic proton region spectra (at 500 MHz) of Act D-d(ATGCAT) mixtures at various drug:DNA ratios as indicated in the plot (a-e), and from d(ATGCAT), THP(A) and THP(B) mixtures at molar ratios of 1:30:30 and Act D at various drug:DNA ratios, as indicated in the plot (a'-e'). Expanded views of (a) and (a') are shown in spectra (A) and (A'), respectively of FIG. 4(b). The spectra were obtained at pH 7 (as in FIG. 3). The proton resonances of the Act D-d(ATGCAT) are indicated in the spectra:adenosine (internal) H2 proton at 8.03 and 8.00 ppm, adenosine (terminal) H2 protons at 7.86 ppm, and guanosine H8 protons at 7.70 and 7.63 ppm. The chemical shifts assignments of Act D-d(ATGCAT) were as in Brown et al. (1984).

Figure 5:
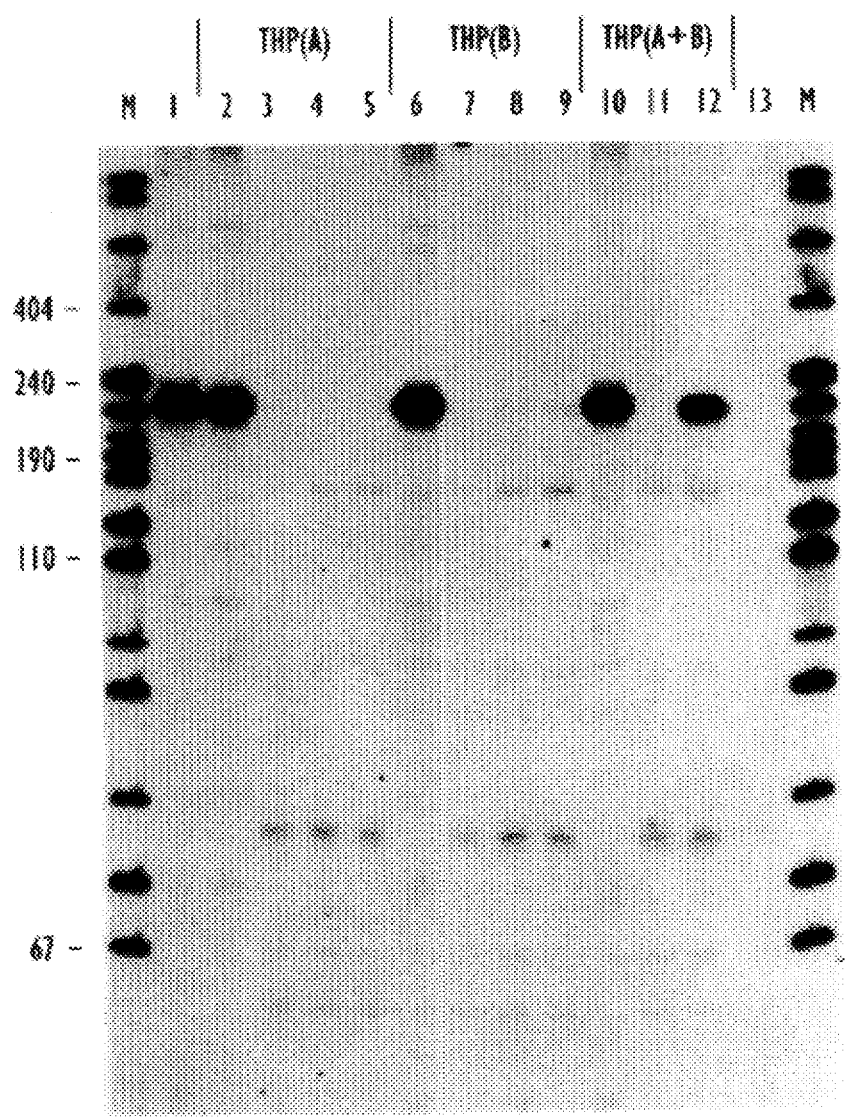

FIG. 5 is a radiogram showing the inhibition of RNA polymerase II transcription by Act D and its resumption due to the addition of THP(A) and THP(B). The constituents of each lane are indicated in Table 6. Relative intensities of the bands were determined as in Table 6. The concentration of the DNA was 71.4 µM.

Figure 6:
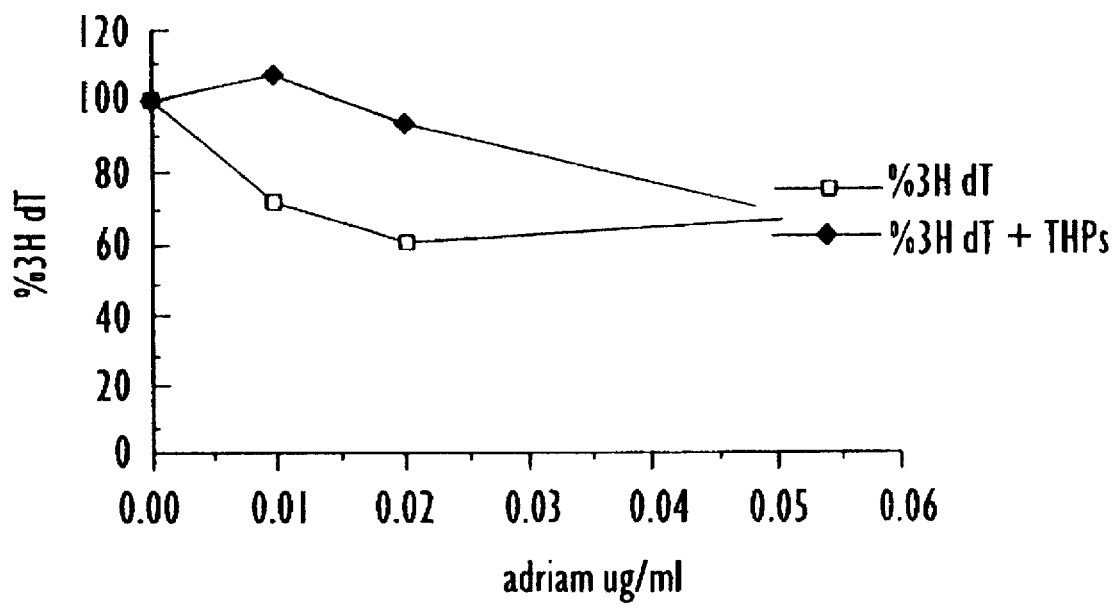

FIG. 6 illustrates reversal of adriamycin inhibition of DNA synthesis due to THPs. It depicts a schematic presentation of percent [$^3$H] thymidine incorporated versus adriamycin concentration according to the table below the scheme. Empty squares—[$^3$H] thymidine incorporation versus adriamycin concentration. Filled squares—[$^3$H] thymidine incorporation versus adriamycin concentration in the presence of THPs (100 µg/ml).

Figure 7:
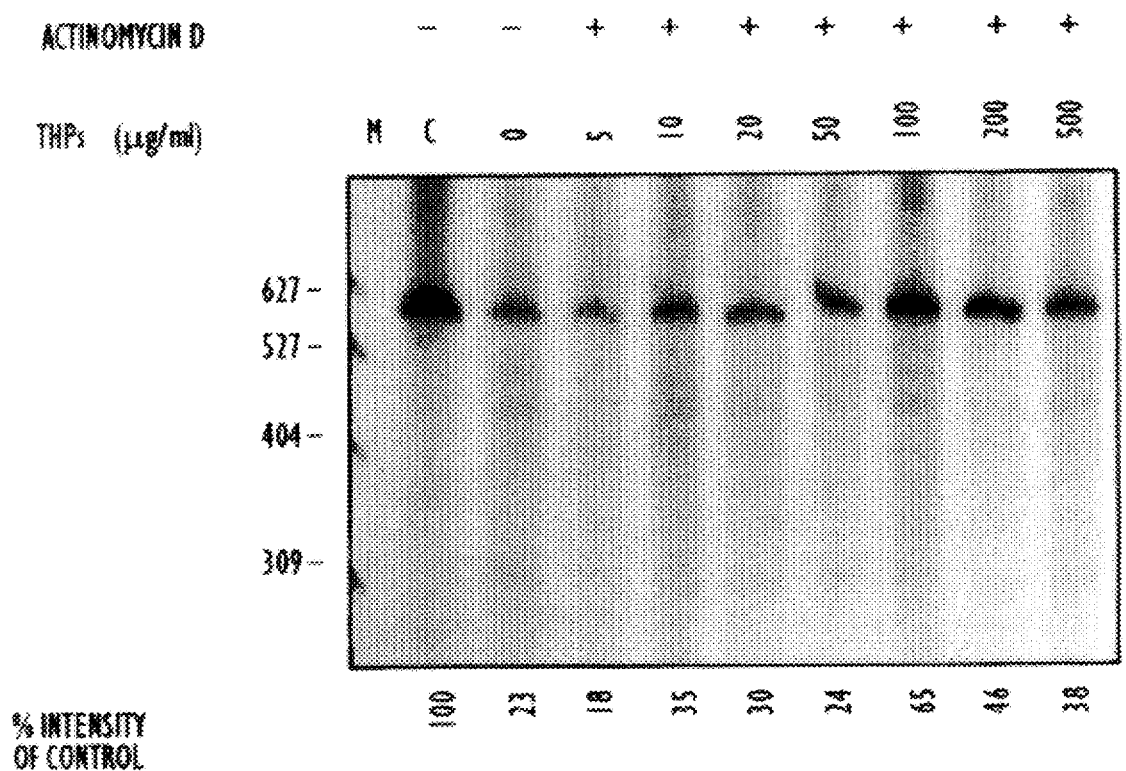

FIG. 7 illustrates reversal of actinomycin inhibition of transcription due to THPs using the HeLa WCE system. Transcription under pulse chase conditions was performed as described in Example 6. The DNA was preincubated with THPs (A+B) at increasing concentrations for 20 min at 30° C., actinomycin D was then added at a concentration of 0.4 µg/ml. Following 20 min of incubation, WCE (10 µl) was added for incubation of 20 min at 30° C. Radioactive nucleotide mix was then added for a pulse of 5 min followed by addition of chase mix containing 10 mM CTP. Transcription proceeded for 30 min at 30° C. and was then stopped. RNA was extracted and analyzed as described in Example 6. Lane M—molecular weight markers. Lane C—control reaction without adriamycin or THPs. Lanes of reaction with 0.4 µg/ml actinomycin D are marked (+), lanes of increasing concentrations of THPs (0, 5, 10, 20, 50, 100,, 200, 500 µg/ml) are also marked above the lanes. The relative intensities of the bands were estimated as described in Example 6 and the percent is of the control (lane C).

Figure 8:
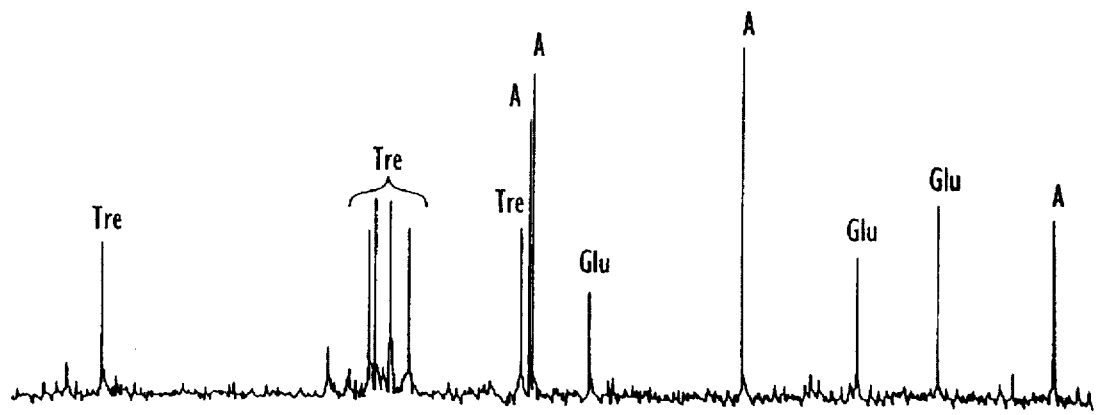
Figure 8:
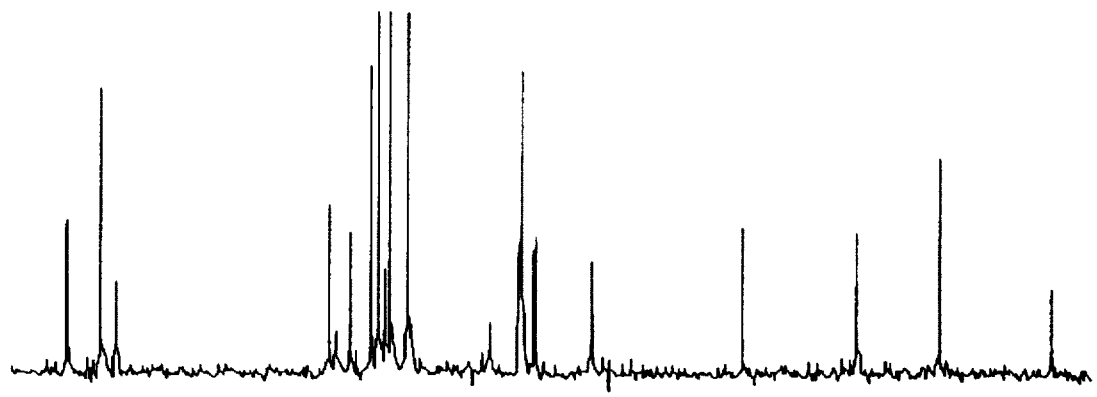
Figure 8:
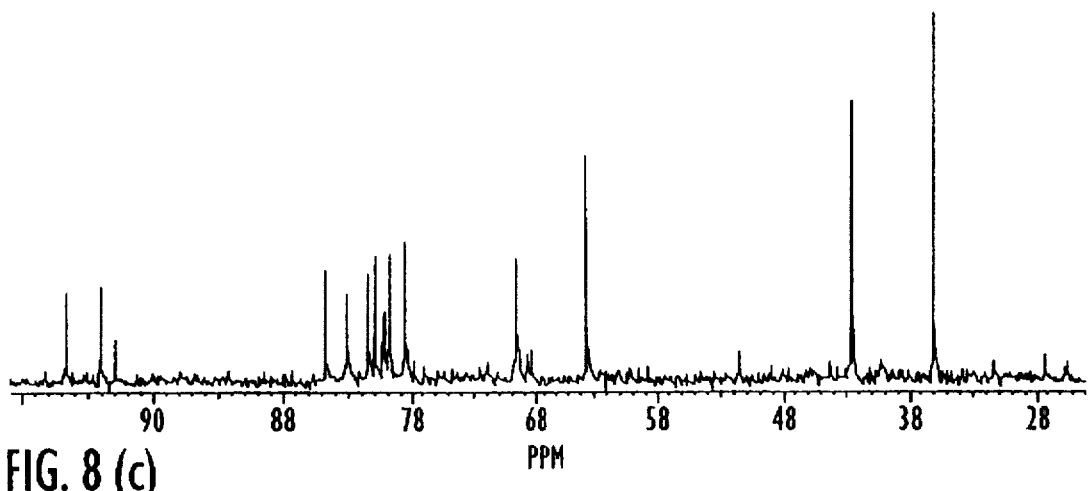

FIG. 8 shows proton-decoupled natural abundance $^{13}$C NMR (126.7 MHz) spectra of extracts from S. clavuligerus cells grown in chemically defined medium at different salt concentrations. (A) 0.5M NaCl. (B) 0.25M NaCl. (C) no salt. The $^{13}$C peaks include the following : A. THP(A); Tre, trehalose; Glu, glutamic acid.

Figure 9:
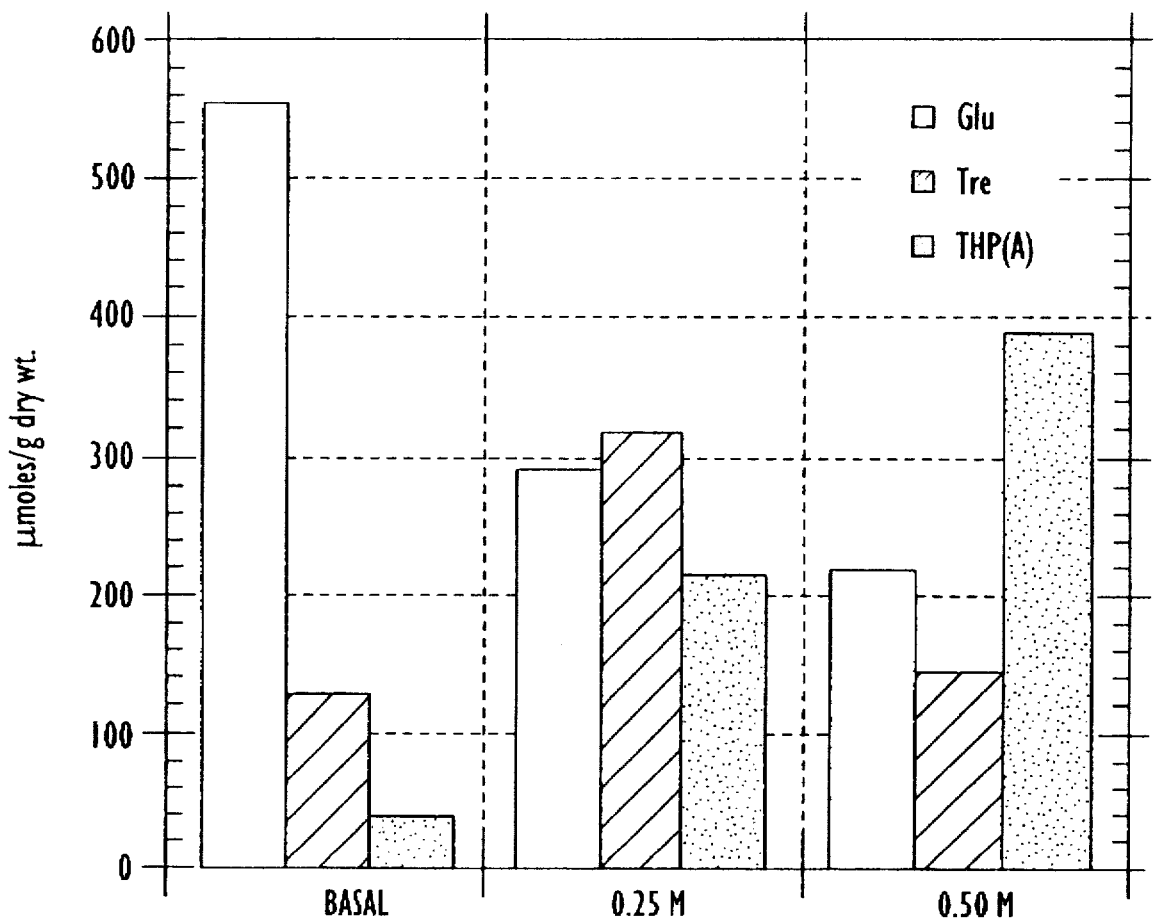

FIG. 9 shows intracellular metabolites in S. clavuligerus cells grown in the chemically defined medium at various salt concentrations as calculated from the NNR spectrum shown in FIG. 8. Glutamic acid was measured by amino acid analyzer, and values for THP(A) and trehalose were computed by integration from NMR spectra.

Figure 10:
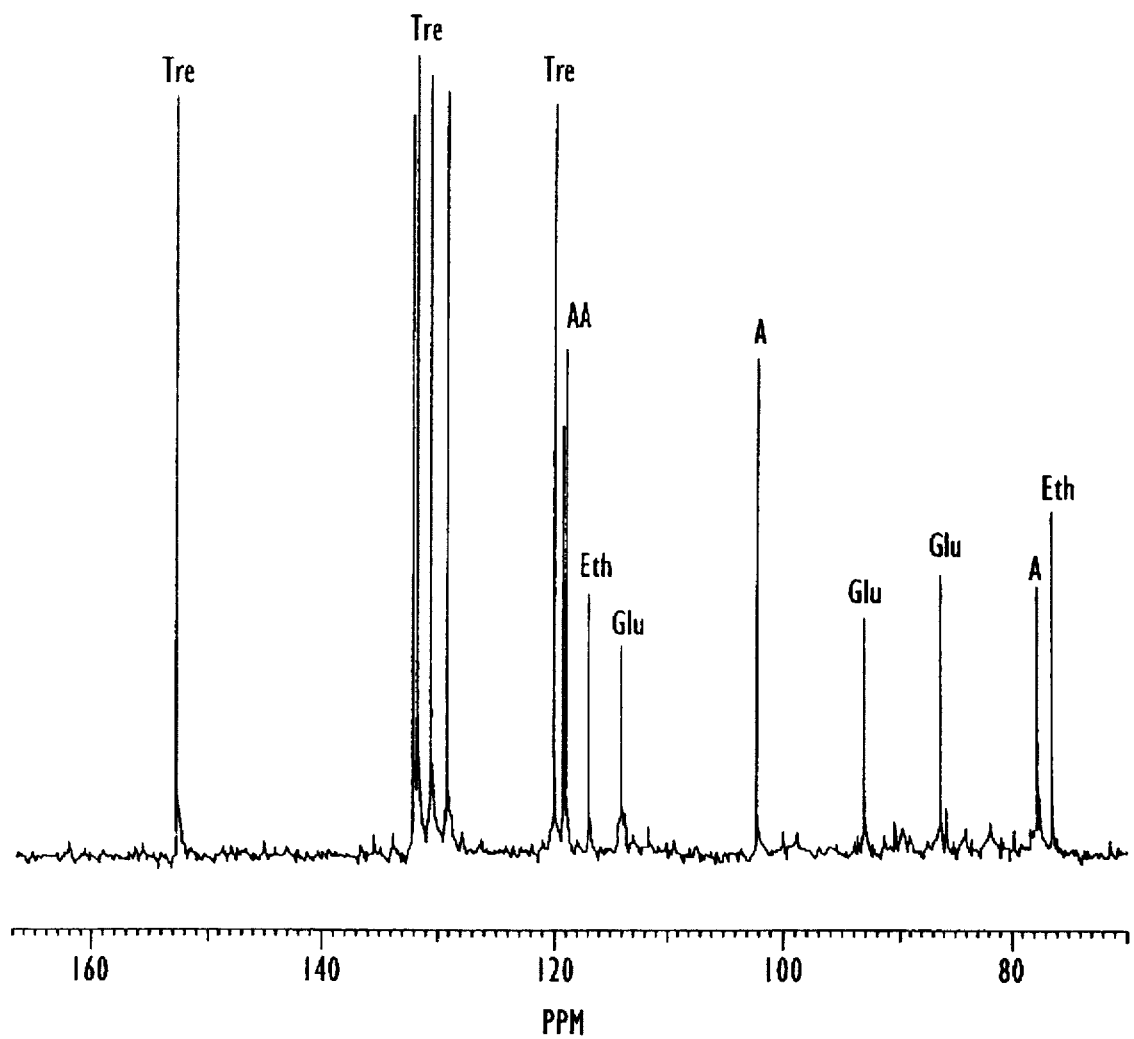

FIG. 10 shows proton-decoupled $^{13}$C NMR (126.7 MHz) spectrum of extracts from S. griseus cells grown in chemically defined medium with 0.5M of NaCl for 66 hours. The $^{13}$C peaks include the following: A—THP(A); Tre—trehalose; Glu-glutamic acid; Eth—ethanol (added for quantitative measurement of THP(A)).

Figure 11:
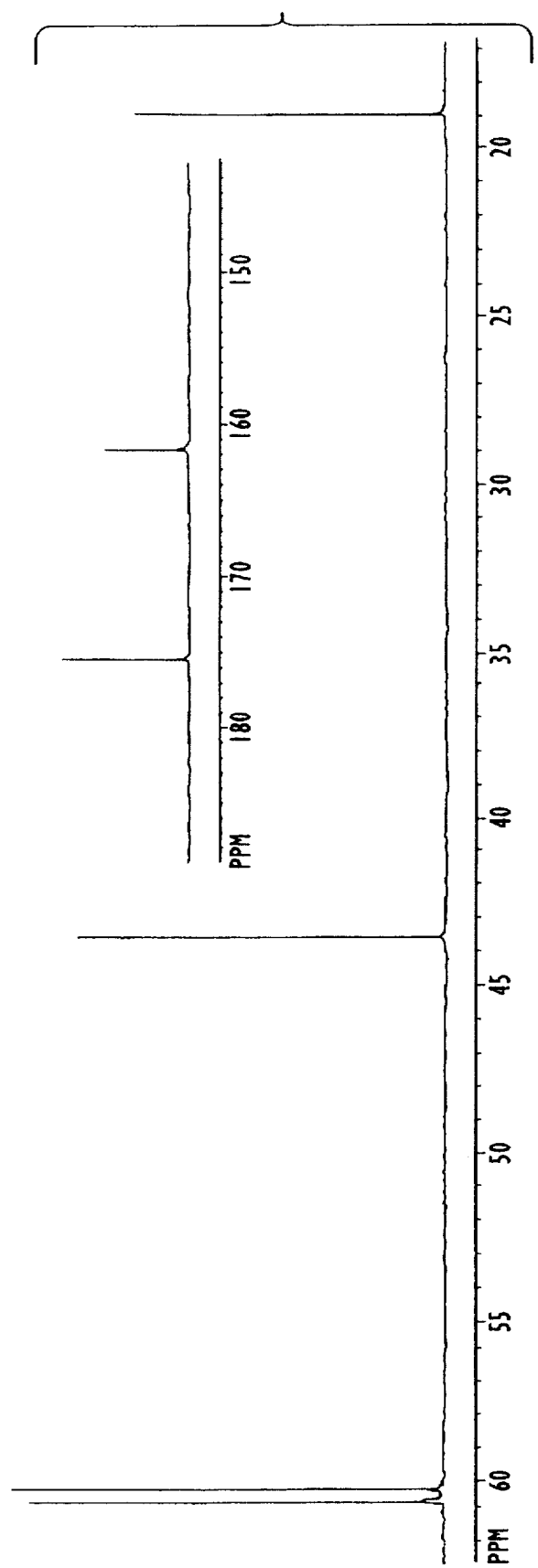

FIG. 11 shows proton-decoupled $^{13}$C NMR (126.7 MHz) spectrum of purified THP(A) obtained from S. griseus.

The invention is further illustrated by the following non-limiting examples:

EXAMPLES

Example 1

Isolation and purification of THP(A) and THP(B) from cell extracts of S. parvalus ATCC 12434.

(a) Cultivation of growth culture

S. parvulus (ATCC 12434), kept on soil culture at 4° C., was grown on NZ amine medium (Sheffield Chemicals, N.Y., USA) for 2 days at 30° C. in a gyratory shaking incubator. After centrifugation and washing twice with 0.3% KCl, a suspension of the mycellium (3%) served as inoculum for the chemically defined growth medium (40 g D-fructose, 1.0 g $K_2HPO_4$, 25 mg $ZnSO_4.7H_2O$; 25 mg $CaCl_2.2H_2O$; 25 mg $MgSO_4. 7H_2O$; 25 mg $FeSO_4.7H_2O$, and 2.1 g L-glutamic acid/1000 ml of deionized water at pH 7.1).

(b) Cell Extract Preparation

Extracts of S. parvulus cells were prepared from 1 liter of S. parvulus growth culture. Cells were harvested by centrifugation (at 5,000×g for 5 min) at about 4° C. Cells were washed twice with 0.2% KCl solution to remove traces of culture medium. Intracellular extracts were obtained either by suspending washed cell pellets in 10 ml of water and heating them for 15 min at 100° C., or by the perchloric acid procedure (Inbar and Lapidot, 1988a). The supernatant was separated by centrifugation at 15,000×g for 15 min and concentrated under reduced pressure to 1 ml.

(c) Separation of THP(A) and THP(B) from S. parvulus cell extracts

Cell extract samples were mixed with 4 volumes of 1M acetic acid before separation by Dowex 50 W chromatography. The column was washed with deionized water (five times the column volume) to remove carbohydrates and polyols. Amino acids, THP(A) and THP(B) were eluted with 3M $NH_4OH$. Ammonia was evaporated to dryness and the residue was brought to pH 5 and separated by Dowex 1 anion exchange (acetate-form) chromatography. Acidic amino acids such as glutamic acid remained attached to the anion exchange column. THP(A) and THP(B) were eluted with water.

(d) Separation of THP(A) and THP(B) from peptides and proteins

The mixture of THP(A) and THP(B) obtained in step (c), was added to a 40 ml column of Sephadex G-25. The column was washed with water. The first fractions consisted of peptides and low molecular weight proteins (yellow in color), and THP(A) and THP(B) were next eluted.

(e) Separation of THP(A) from THP(B).

Figure 1A:
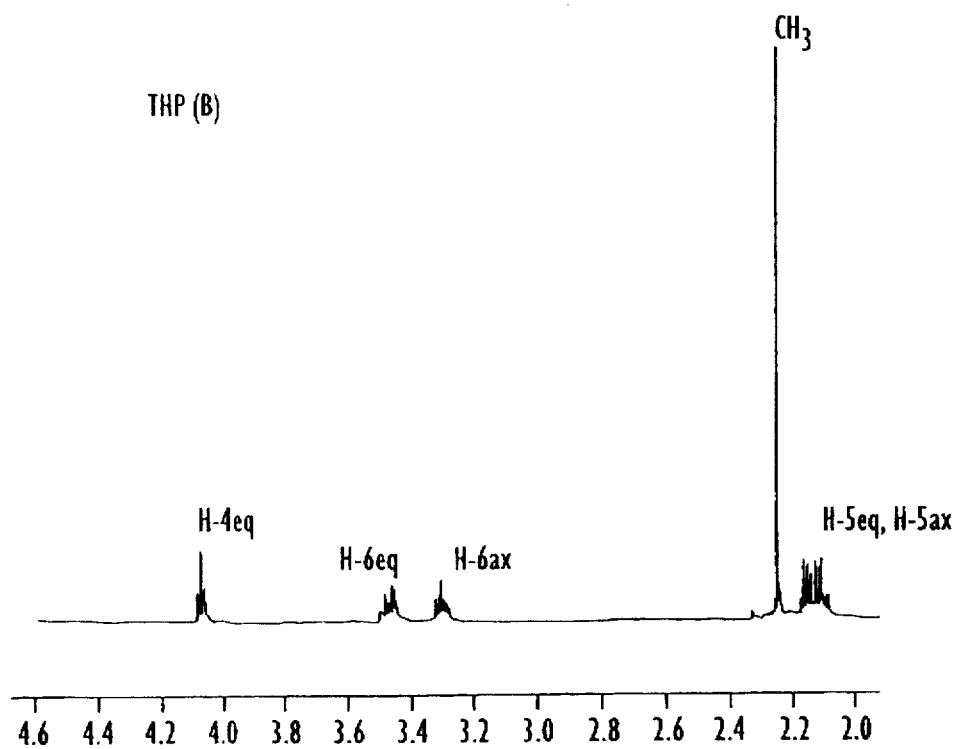
FIG. 1 depicts the (500-MHz)$^1$H NMR spectra of (a) purified THP(B) and (b) purified THP(A).
Figure 1B:
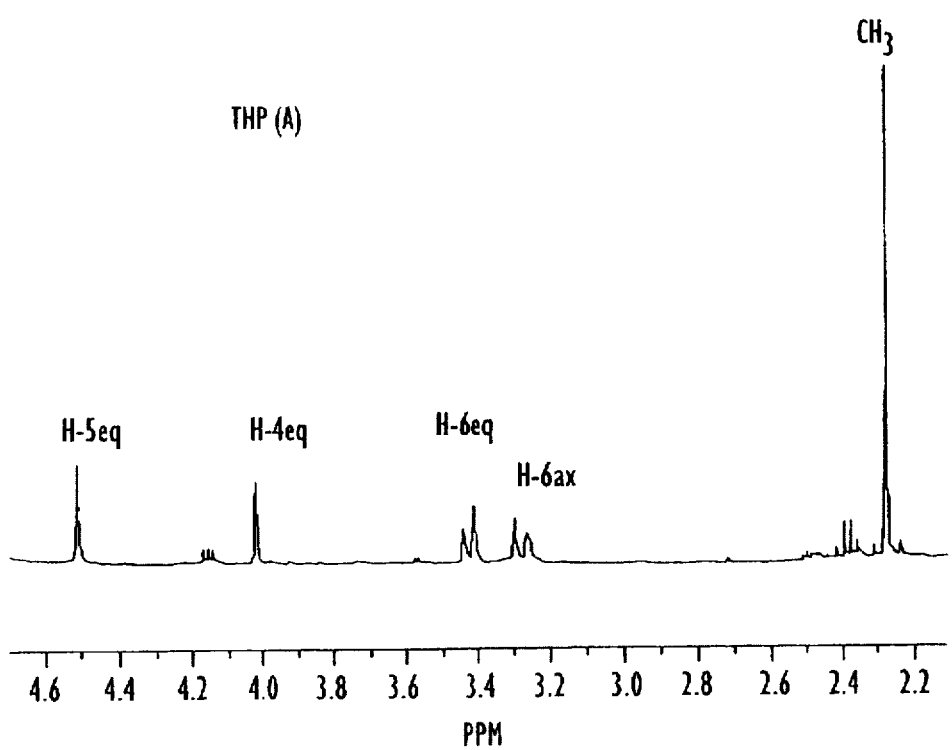
Figure 2:
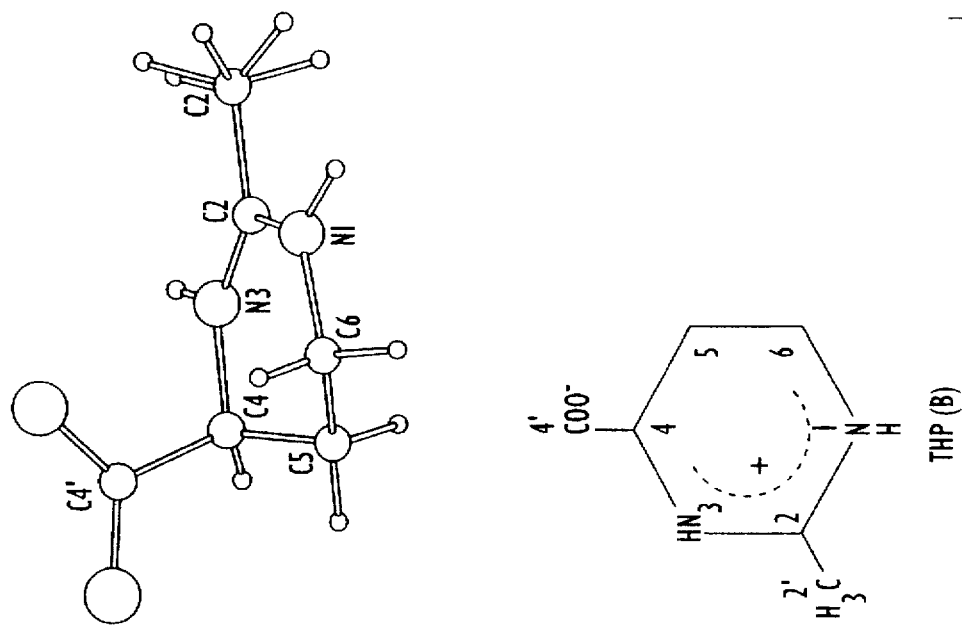
FIG. 2 depicts the molecular structures and stereochemical configurations (S form) of THP(A) and THP(B).
Figure 2:
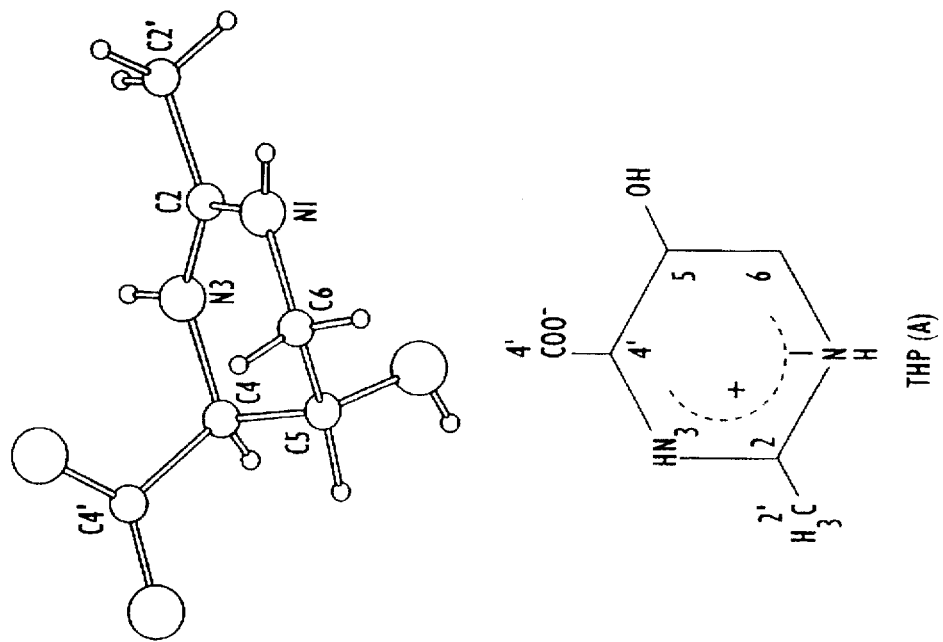

The mixture of THP(A)+THP(B) obtained in step (d) was mixed with 4 volumes of 1M acetic acid before adding to a 70 ml column of Dowex 50 W×8 ($NH_4^+$ form). THP(A) together with a small amount of THP(B) were eluted with water. THP(B) together with a small amount of THP(A) were displaced with 3M ammonium hydroxide. By repeating these procedures once more, complete separation of THP(A) from THB(B) was obtained. The fraction of THP (B) contained also a small amount of alanine. The latter fraction was brought to pH 2 (with HCl) and separated on a 70 ml column of Dowex 1 anion exchange (OH- form) chromatography. The column was washed with water and THP(B) was displaced with 150 ml of 1% formic acid (alanine was eluted with 600 ml of 1% formic acid). The $^1H$ NMR spectra of purified THP(A) and THP(B) are shown in FIG. 1 (b) and (a), respectively. The molecular structures are shown in FIG. 2.

Example 2
Crystallization of THP(A) and THP(B).$2H_2O$ (a) Pure THP(A) obtained according to Example 1 was dissolved in hot methanol and the solution was left in a desiccator under benzene vapor for crystallization. Crystals appeared after 7 days. The transparent, prismatic crystals having the dimensions 0.2×0.1×0.05 mm were collected for X-ray crystal structure analysis. Crystal structure of ($C_6H_{10}N_2O_3$), trigonal with space group $P3_1$ was found. The bond lengths and bond angles of the crystals are presented in Tables 1 and 2, respectively. The stereochemical configuration of THP(A) was found to be the S form.

(b) Pure THP(B) obtained according to Example 1 was dissolved in ethanol and a few drops of methylene chloride were added to the solution. The solution was left to evaporate slowly. After a few days, crystals appeared in the solution. The transparent prismatic crystals having the dimensions 0.4×0.3×0.2 mm were collected for X-ray crystal structure analysis. Crystal structure of $C_6H_{10}N_2O_2.2$ |$H_2O$| is tetragonal with space group $P4_3$. The bond lengths and bond angles of the crystals are presented in Tables 1 and 2, respectively. The stereochemical configuration of THP(B) was found to be the S form.

TABLE 1

| Bond lengths (Å) | | | |
|---|---|---|---|
| THP(B) | | THP(A) | |
| C(2)-N(1) | 1.303 (4) | C(2)-N(1) | 1.311 (10) |
| C(2')-C(2) | 1.487 (4) | N(3)-C(2) | 1.310 (8) |
| C(4)-N(3) | 1.459 (4) | C(4)-N(3) | 1.458 (9) |
| C(5)-C(4) | 1.522 (4) | C(4')-C(4) | 1.545 (11) |
| O(8)-C(4') | 1.260 (3) | O(9)-C(5) | 1.405 (10) |
| C(6)-N(1) | 1.456 (4) | O(8)-C(4') | 1.217 (10) |
| N(3)-C(2) | 1.312 (4) | C(6)-N(1) | 1.462 (9) |
| C(4')-C(4) | 1.529 (5) | C(2')-C(2) | 1.499 (10) |
| O(7)-C(4') | 1.247 (4) | C(5)-C(4) | 1.527 (12) |
| C(6)-C(5) | 1.508 (5) | C(6)-C(5) | 1.519 (10) |
|  |  | O(7)-C(4') | 1.272 (9) |

TABLE 2

| Bond angles (degree) | | | |
|---|---|---|---|
| THP(B) | | THP(A) | |
| C(6)-N(1)-C(2) | 123.7 (3) | C(6)-N(1)-C(2) | 121.5 (6) |
| N(3)-C(2)-N(1) | 121.5 (3) | C(2')-C(2)-N(1) | 118.1 (6) |
| C(4)-N(3)-C(2) | 122.4 (3) | C(4)-N(3)-C(2) | 124.2 (6) |
| C(5)-C(4)-N(3) | 108.9 (3) | C(4')-C(4)-N(3) | 113.5 (7) |
| O(7)-C(4')-C(4) | 116.5 (3) | C(6)-C(5)-C(4) | 109.4 (7) |
| O(8)-C(4')-O(7) | 126.0 (3) | O(9)-C(5)-C(6) | 108.8 (6) |
| C(5)-C(6)-N(1) | 109.1 (3) | O(7)-C(4')-C(4) | 111.9 (7) |
| C(2')-C(2)-C(2') | 118.8 (3) | O(8)-C(4')-O(7) | 127.8 (7) |
| N(3)-C(2)-C(2') | 119.7 (3) | N(3)-C(2)-N(1) | 121.7 (7) |
| C(4')-C(4)-N(3) | 112.9 (3) | C(2')-C(2)-N(3) | 120.2 (7) |
| C(5)-C(4)-C(4') | 110.4 (3) | C(5)-C(4)-N(3) | 109.5 (6) |
| O(8)-C(4')-C(4) | 117.5 (3) | O(9)-C(5)-C(4) | 111.3 (6) |
| C(6)-C(5)-C(4) | 109.6 (2) | C(5)-C(6)-N(1) | 108.6 (6) |
|  |  | O(8)-C(4')-C(4) | 120.2 (6) |

Example 3
Binding of Act D to oligonucleotide in the presence of THP(A) and THP(B)—NMR studies Characterization of the binding of Act D with DNA has been the subject of considerable interest since this is the presumed basis of its antitumor activity. It seems clear that the peptide chains pendant on the phenoxazone ring are largely responsible for the preference of the binding of Act D at GpC sites of DNA. Detailed solution structure modeling investigations have been carried out on the 1:1 complex of Act D and d(ATGCAT) (Lybrand et al., 1986).

The mode of binding of THPs to DNA in the presence and absence of Act D was investigated by $^1H$ NMR spectroscopy. The oligonucleotide d(ATGCAT) was selected for this study for several reasons: it contains a unique strong binding site for Act D, it is long enough to interact with the pentapeptide lactones of Act D, and the kinetics of Act D-d(ATGCAT) association are slow and mimic the kinetics of Act D-DNA association (Brown et al., 1984; Zhou et al., 1989). $^1H$ NMR studies conducted on DNA-THP (A) and (B) complexes indicate that THP(A) and THP(B) bind the oligonucleotide and largely prevent its complex formation with Act D.

(a) Binding of THPs to d(ATGCAT). A comparison of the chemical shifts of the non-exchangeable protons in the free d(ATGCAT) and in complexes of d(ATGCAT) with THP(A) and THP(B) are shown in Table 3. On addition of THP(A) and THP(B) to the hexamer, the guanosine H8 (GH8) signal at 7.94 ppm exhibited the major downfield chemical shift (20 Hz), the adenosine (terminal) H8 protons moved downfield by 10 Hz, while all the other base aromatic protons exhibited only minor changes.

(b) Binding of THPs to the Act D-d(ATGCAT) complex. On addition of THP(B) to the complex of Act D-d (ATGCAT) (at a molar ratio of 0.64 Act D per hexamer), the chemical shift of GH8 protons moved downfield by 0.018 ppm, while the chemical shift of the adenosine (internal) H2 proton of the Act D-hexamer complex at 7.99 ppm remained unchanged (FIG. 3b). When THP(A) was added, an additional downfield shift (0.22 ppm) of GH8 protons was noted (FIG. 3c). These results indicate that THPs bind the free oligonucleotide even in the presence of Act D.

(c) Binding of Act D to d(ATGCAT). The binding of Act D to free oligonucleotide and to the oligonucleotide-THPs complex have been investigated by the $^1$H NMR titration technique. On addition to 0.16 molar equiv. of Act D to the hexamer, new proton peaks of the complex appeared (FIG. 4b) and their intensities increased up to 1:1 Act D to d(ATGCAT) (FIG. 4a, b, c, d, e). The signal ratios of free hexamer and hexamer bound to Act D are shown in Table 4.

(d) Binding of Act D to the d(ATGCAT)-THPs complex.

When 0.16 molar equiv. of Act D was added to the hexamer-THPs complex, no new proton peaks of the Act D-hexamer complex appeared (FIG. 4b'); on addition of 0.32 molar equiv. of Act D, only one proton peak of Act D-hexamer complex was detectable at 8.03 ppm (FIG. 4c'). Only when 0.48 molar equivalent of Act D was added to the hexamer-THPs, could most of the new proton peaks of the Act D-hexamer be distinguished, as shown in FIG. 4d',e'. Two resonances of the Act D-hexamer are missing, the signal of the adenosine (internal) H2 of the Act D-hexamer complex at 7.99 ppm could not be detected due to the intense resonance of GH8 of the THPs-hexamer complex at 7.98 ppm, while the resonance of adenosine (terminal) H2 at 7.87 ppm of the Act D-hexamer complex was obscured by the coincident resonance of the NH proton of THP(B) at 7.88 ppm. The equilibrium binding properties of Act D-d (ATGCAT) in the presence and absence of the THPs (Table 4) were derived from the proton peak area ratios of the free hexamer to the bound Act D-hexamer. Due to difficulties in obtaining precise binding data at low values of Act D bound to the hexamer, binding constants could not be determined. However, equilibrium measurements (FIG. 4 and Table 4) demonstrate the potential activity of THPs in protecting DNA from Act D intercalation by some kind of binding to DNA, probably by a mechanism competitive with the antibiotic.

TABLE 3

Base proton chemical shift assignments (ppm) of nonexchangeable protons of d(ATGCAT) and d(ATGCAT) - THP(A) + THP(B)

| Assign't | d(ATGCAT) δ1 | THP(A) + THP(B) - d(ATGCAT) δ2 | Difference δ1-δ2 |
|---|---|---|---|
| $A_i^8$ | 8.330 | 8.330 | 0.000 |
| $A_t^8$ | 8.186 | 8.203 | +0.017 |
| $G^8$ | 7.944 | 7.984 | +0.040 |
| THP(A) |  | 7.913 | 0.000 |
| $A_i^2$ | 7.908 | 7.908 | 0.000 |
| THP(B) |  | 7.881 |  |
| $A_t^2$ | 7.844 | 7.849 | +0.005 |
| $C^6$ | 7.368 | 7.376 | +0.008 |
| $T_i^6$ | 7.356 | 7.356 | 0.000 |
| $T_t^6$ | 7.251 | 7.256 | +0.005 |

Adenosine (internal H8 ($A_i^8$); adenosine (terminal) H8 ($A_t^8$); guanosine H8 ($G^8$); adenosine (internal) H2 ($A_i^2$); adenosine (terminal) H2 ($A_t^2$) cytosine H6 ($C^6$); thymine (internal) H6 ($T_i^6$) and thymine (terminal) H6 ($T_t^6$).

TABLE 4

Equilibrium binding of Act D to d(ATGCAT) in the presence and absence of THPS

| Molar ratio of Act D/d(ATGCAT) | d(ATGCAT) (free/bound)[a] | d(ATGCAT) - THPs (free/bound)[a] |
|---|---|---|
| 0.16 | 4.9 | n.d. |
| 0.32 | 1.7 | 3.5 |
| 0.48 | 0.8 | 2.7 |
| 0.64 | 0.4 | 1.3 |

(a) Proton peak area ratios of free hexamer $A_i^8$ (two protons/2): bound Act D-hexamer $A_i^2$ (one proton).
n.d. - non-determined.

Example 4

In vitro transcription studies in the presence of Act D: the protection effect of THP(A)+THP(B)

(a) Transcription inhibition by Act D

The inhibition of RNA polymerase transcription caused by Act D binding to DNA was studied using the system described in Kadesch and Chamberlin, 1982, in which purified RNA polymerases from mammalian cells, such as RNA polymerases I, II and III from HeLa cells, are able to transcribe defined dCMP-tailed DNA templates efficiently and specifically. The dCMP-tailed DNA system allows quantitative studies of transcription reactions by the polymerase protein itself in the absence of other protein factors, and is thus an appropriate system to analyze the direct effect of DNA-binding drugs on the transcription process, and the protective effect of THP(A) and THP(B) on transcription in the presence of Act D.

DNA-dependent RNA polymerases I, II and III from HeLa cells (pol I, pol II and pol III, respectively) were purified by a method which is a modification of the procedure described by Hodo and Blatti, 1977.

The templates DNA were linearized by restriction enzyme Pst I generating a 3' protruding end, and tailed at both ends with dCTP by using terminal transferase (Boehringer Mannheim). Following ethanol precipitation, the dCMP-tailed DNAs were digested with a second restriction enzyme, and the selected tailed fragment was purified from agarose gel as described by Kadesch and Chamberlin, 1982.

Transcription reaction mixtures were incubated in 15 µl of transcription buffer containing 70 mM Tris-HCl (pH 7.9), 0.1M NH$_4$Cl, 6 mM MgCl$_2$, 5 mM spermidine, 10% glycerol, 0.15 mM dithriothreitol, 0.6 µg of dCMP-tailed template, and 0.5 µl of HeLa RNA polymerase (3u) at 30° C. for 10 min. Pulse buffer (3.5 µl) containing 4.3 mM of ATP, GTP and CTP, and 170 µM UTP, 20 µCi of [α-$^{32}$P]UTP was added to the transcription reaction mixture for 20 seconds incubation. Transcription elongation then took place by adding 1.5 µl of chase buffer containing 7 mM UTP in the presence or absence of 0.06 µg Act D. Transcription elongation was carried out for 10 min and was then stopped by addition of proteinase K buffer (0.6% SDS; 25 mM Tris pH 7.9; 25 mM EDTA final concentration) 200 µg/ml proteinase K, and 30 µg of tRNA, and incubated for 25 min at 65° C. The sample was ethanol precipitated, pellet was resuspended in loading buffer (90% formamide; 0.5×Tris borate buffer) and subjected to 6% polyacrylamide—urea gel electrophoresis. The autoradiogram of the gel was analyzed by molecular dynamics computing densitometer to determine the relative intensities of the bands. (Nucleoside triphosphates and tRNA were purchased from Sigma, proteinase K from Boehringer Mannheim, and [α-$^{32}$P]CTP (400 Ci/mmol) from Amersham International, United Kingdom).

The sensitivity of the three RNA polymerases from HeLa cells to various concentrations of Act D was determined, using the purified polymerases and a dCMP-tailed template of 225 bp for pol I and of 420 bp for pol II and pol III. These templates are expected to give runoff transcripts of 225 and 420 nucleotides, respectively, since RNA polymerase initiates transcription at discrete sites at the single-stranded tail double stranded duplex junction. In all experiments a pulse-chase protocol was used.

The transcription inhibition patterns due to Act D of the three polymerases (pol I, II and III, respectively) are summarized in Table 5 and indicate that the enzymes are similarly sensitive to Act D. When 1 µg/ml Act D is added with the chase, only 10–20% residual transcription occurs, yet at a concentration of 3–5 µg/ml only 0.1–3% residual transcription is obtained.

These findings are in good agreement with the notion that Act D inhibition is dependent on the DNA concentration in the reaction mixture.

TABLE 5

Percentage of residual transcription in the presence of Act D

| RNA Polymerase | Actinomycin-D µg/ml | | | | |
|---|---|---|---|---|---|
| | 0 | 1 | 3 | 4 | 5 |
| I | 100 | 16 | | | 3 |
| II | 100 | 22 | | 3 | 3 |
| III | 100 | 13 | 3 | | 0.1 |

(b) Resumption of Act D inhibited transcription by THP(A) and THP(B)

The assay was performed in a concentration of Act D causing over 97% inhibition of transcription, that was taken as 3 µg/ml. It was figured that the concentration of the THP(A)+THP(B) required to prevent binding of Act D to DNA would be higher than that of Act D, since they are expected to protect the DNA in general and not necessarily at d(GpC) base pair (bp), whereas the concentration of Act D is related to the d(GpC) content of the DNA. As can be seen in lanes 2, 6, 10 of FIG. 5 and in Table 6, in these experiments THP(A) and THP(B) by themselves did not inhibit the transcription reactions. In the presence of either THP(A) alone or THP(B) alone, the inhibition of transcription caused by Act D was not affected (as shown in FIG. 5, lanes 3–5 and 7–9, and in Table 6). Yet when THP(A) and THP(B) were added together in a ratio of 1:1, their effect was dramatic. At a concentration of 200 µM there was a recovery of 75% of transcription in the presence of 2.5 µM Act D, which by itself would have inhibited 97% of the reaction. These results indicate that the combination of THP(A) and THP(B) have a synergistic effect on protection of DNA from Act D binding to the DNA. The conditions described above indicate that inhibition of transcription (97%) is obtained by one molecule of Act D per 30 bp, whereas saturation of DNA-Act D complex formation would have required a ratio of 1:10. In order to recover 75% transcription, 80 molecules of THP(A)+THP(B) per each molecule of Act D are required, or a ratio of one pair of THP(A)+THP(B) per bp. These results suggest the role of THP(A)+THP(B) in protection of DNA against Act D binding, which enables transcription to be resumed in the presence of Act D.

TABLE 6

Residual transcription in the presence of Act D and THP(A) and THP(B)

| Lane No. | THP | | Act D [3 µg/ml] | % |
|---|---|---|---|---|
| | | µg/ml | µM | [2.5 µM] | transcription |
| 1 | control | 0 | 0 | – | 100 |
| 2 | THP(A) | 60 | 400 | – | 100 |
| 3 | THP(A) | 10 | 66 | + | 0.2 |
| 4 | THP(A) | 30 | 200 | + | 0.5 |
| 5 | THP(A) | 60 | 400 | + | 1.5 |
| 6 | THP(B) | 60 | 400 | – | 100 |
| 7 | THP(B) | 10 | 60 | + | 1.0 |
| 8 | THP(B) | 30 | 200 | + | 2.7 |
| 9 | THP(B) | 60 | 400 | + | 5.1 |
| 10 | THP(A + B)(1:1) | 60 | 400 | – | 100 |
| 11 | THP(A + B)(1:1) | 10 | 66 | + | 4.6 |
| 12 | THP(A + B)(1:1) | 30 | 200 | + | 75.0 |
| 13 | THP(A + B)(1:1) | 0 | 0 | + | 0.2 |

Example 5

Cell growth and drug treatment: Reversal of adriamycin inhibition of DNA synthesis due to THPs.

HL60 cells were grown in RPMI medium (Gibco) containing 10% fetal calf serum (Biological Laboratories—Bet Haemek) in microwell plates (Nunc). Cells were suspended in medium at a concentration of $2 \times 10^5$ cells per ml and dispersed into the wells of the plates in 100 µl aliquots. Following 20 hrs of incubation at 37° C., the cells were treated with THPs (100 µg/ml) and adriamycin at increasing concentrations as indicated in FIG. 6. After 24 hrs [$^3$H] thymidine was added (1 µCi/well, 120 µl) for a duration of 3 hrs. Thymidine incorporation was stopped by addition of 25 µl trichloroacetic acid (TCA) at 20%, and the plates were placed at 4° C. overnight. TCA precipitates were washed with 10% TCA (100 µl), solubilized in 100 µl 1N NaOH and transferred to vials for counting in the presence of 3 ml scintillation solution containing toluene:Lumax (Lumac, The Netherlands) (3:2) mix. Assays were performed in triplicates.

As can be seen in FIG. 6, when HL60 cells are treated with adriamycin at concentrations of 0.01–0.02 µg/ml [$^3$H] thymidine incorporation is inhibited by 30–40%, respectively. Addition of THPs (A+B) (at a ratio of 1:1) at final concentration of 100 µg/ml reverses the inhibitory effect of adriamycin so that in spite of the presence of adriamycin (0.01–0.02 µg/ml) [$^3$H] thymidine incorporation is very efficient, 107%–93%, respectively. This result gives further indication that the THPs may protect DNA from damaging drugs.

Example 6

In vitro transcription using HeLa whole cell extract (WCE): Reversal of actinomycin D inhibition of transcription due to the presence of THPs.

WCE was prepared according to Manley, 1984. A 20-µl reaction contained 10 µl WCE, 1 µg DNA, 4 mM creatine phosphate, 500 µM ATP, GTP, UTP, 50 µM CTP, 20 µCi of [α-$^{32}$P]CTP, and transcription was performed at 30° C. All reactions were preincubated 20 min before the addition of the nucleotide mixture; 3 min after the addition of radioactive nucleotides, (pulse), chase mix containing 10 mM unlabelled CTP was added and transcription proceeded for additional 20 min. Reactions were stopped and RNA was analyzed as in Example 4.

In a preliminary experiment, the degree of transcription inhibition by actinomycin D in the HeLa-WCE system was checked. A concentration of 0.4 µg/ml was used, which gave about 80% inhibition. In the experiment presented in FIG. 7, it is clear that Act D alone at 0.4 µg/ml inhibits the transcription reaction by 80% (compare lane 0 to lane C). Addition of low concentrations of THPs do not affect the reaction up to 20 µg/ml, whereas at concentrations of 100–200 µg/ml there is resumption of transcription up to 40–65% of the control. This experiment indicates that THPs (A+B) may reverse the Act D inhibition of transcription resuming transcription by about 25%–45% above the residual 20% of transcription caused by actinomycin D alone.

These results further indicate that THPs may protect the DNA from drugs that bind to it. Thus THPs cause reversal of the inhibitory effects of DNA binding drugs and enable efficient nucleic acid synthesis by polymerases in spite of the presence of the drugs.

from endonuclease digestion is comparable to the amounts of actinomycin D and distamycin A that bind to DNA, as described before (Nosikov et al., 1976 and 1977).

It is noteworthy that while DNA is protected by THPs from digestion by restriction endonucleases, the activity of RNA polymerase is not affected either by THP(A) or THP(B), or both, as shown by the inventors of the present invention. This difference may arise from the mode of binding of the two enzymes. RNA polymerase binds to duplex DNA and searches for a promoter site by forming transient hydrogen bonds with exposed hydrogen donor and acceptor groups of base pairs, whereas EcoRI endonuclease recognizes its palindrome target site without breaking base pairs but through electrostatic attraction to the phosphate backbone of the DNA.

TABLE 7

Protection of the DNA by THPs from restriction enzymes' attack

| Restriction Endonuclease | Restriction site | No. of sites | THP(A) inhibition | | | | THP(A) + (B) inhibition | | | | Relation of THP(A)* / THP(A) + (B) |
|---|---|---|---|---|---|---|---|---|---|---|---|
| | | | partial | | complete | | partial | | complete | | |
| | | | µ/ml | mM | µ/ml | mM | µ/ml | mM | µ/ml | mM | |
| EcoRI | 5'GAATTC 3'CTTAAG | 1 | 100 | 0.66 | 1000 | 6.6 | 100 | 0.66 | 250 | 1.66 | 4 |
| AvaI | 5'-CCCGGG 3'-GGGCCC | 1 | 25 | 0.166 | 300 | 1.98 | 25 | 0.166 | 150 | 0.99 | 2 |
| DraI | 5'-TTTAAA 3'-AAATTT | 3 | 100 | 0.66 | 300 | 1.98 | 100 | 0.66 | 150 | 0.99 | 2 |

Example 7

DNA protection by THPs from digestion by restriction enzymes.

Further evidence of the functional interaction of THPs and DNA stems from our finding that a mixture of THP(A) and THP(B), and THP(A) alone, are able to protect a plasmid DNA (pGEM10, Promega) from digestion by restriction endonucleases (EcoRI, AvaI and DraI). The THPs interact with DNA and effectively (at $10^{-4}$M) protect the cleavage sites recognized by the restriction endonucleases. The results are summarized in Table 7.

THPs were added to the digestion mixture to a final concentration as indicated in Table 7. One µg of pGEM10 was subjected to digestion with 0.2–1µ of enzyme in a final volume of 20 µl buffer as recommended by the supplier (New England Biolabs) for 3 hrs. At the end of the incubation time, 5 µl of stop buffer containing 75% glycerol, 3% bromophenol blue and 10 mM EDTA were added and 12 µl of the reaction mix were loaded onto 1% agarose gel. The gel was stained with ethidium bromide (0.5 µg/ml), visualized by UV and photographed. The relative intensities of the bands in the photographs were analyzed by molecular dynamics computing densitometry.

The minimal amount of THP(A)+THP(B) needed to protect DNA from digestion by restriction endonucleases is in the range of 25 to 100 µg/ml, whereas 150 to 250 µg/ml was needed for complete inhibition. From the comparison of AvaI and DraI in the presence of both THP(A) and (B), it seems that AvaI activity is 4 times more sensitive to the inhibitory effect of the THPs. This finding is probably the result of high affinity of THPs to GC residues of AvaI sites in comparison to AT residues of DraI sites (see Table 7). The range of THP(A)+(B) concentration needed to protect DNA Example 8

Isolation and purification of THP(A) from cell extracts of S. clavuligerus.

(a) Cultivation of growth culture.

S. clavuligerus (NRRL 3585) was grown in conditions similar to S. parvulus as described in Example 1(a) above.

S. clavuligerus spores suspension in 20% glycerol was kept at −20° C. Seed culture was inoculated by 100 µl of spore suspension and was grown for 2 days at 30° C. in a gyratory shaking incubator (210 rpm) in the chemically defined medium supplemented with 0.1% NH$_4$Cl and 0.1% of yeast extract. After centrifugation and washing twice with 0.9% NaCl, a suspension of vegetative mycellium (5%) served as inoculum for the chemically defined growth medium. The growth media contained: 1.0% glycerol, 0.2% L-asparagine, 0.06% MgSO$_4$, 0.35% K$_2$HPO$_4$ and 0.68% KH$_2$PO$_4$ and 2 ml of trace salts stock solution per liter. Trace salts stock solution contained 100 mg FeSO$_4$×7H$_2$O, 100 mg MnCl$_2$×4 H$_2$O, 100 mg ZnO$_4$×4H$_2$O, and 100 mg CaCl$_2$ per 100 ml of water. Cells were cultivated in 250 ml Erlenmeyer flasks containing 50 ml medium at 30° C. and 240 rpm on a rotary shaker. THP(A) was accumulated intracellularly when NaCl was added to the basal medium at 0.025M and 0.5M. The trace amount of THP(A) (FIG. 8) found initially by $^{13}$C NMR (FIG. 9) in S. clavuligerus cells grown in 0.05M NaCl, markedly increased to 400 µmol/gr dry wt in 0.5M NaCl. THP(A) was the predominant constituent of the intracellular pool, and its concentration was almost as high as that in the halophilic bacteria grown in 3M NaCl. Thus the machinery of synthesis of THP(A) and THP(B) exist in Act D-producing streptomyces species as a response to actinomycin synthesis, and THP(A) in β-lactam producing S. clavuligerus as a response to changes in salinity.

S. clavuligerus can tolerate 0.5M of NaCl in a minimal liquid medium. Increasing salinity of the medium from 0.05M to 0.5M affected growth rate, while the steady-state level remained the same as in the basal medium. Antibiotic production was extremely sensitive to salinity of the medium and was completely suppressed at 0.25M of NaCl. Metabolic response studied by natural abundance $^{13}$C NMR revealed a 10-fold increase of THP(A) (in comparison to basal medium) and accumulation of trehalose, while the level of intracellular glutamate was decreased (FIGS. 8, 9). Maximal accumulation of intracellular THPs was observed in the midlogarithmic phase of growth and was proportional to increase of NaCl concentration (400 µmol/dry cell wt. of THP(A) at 0.5M NaCl). THP(A) was consumed after 86 hours of growth (late logarithmic phase).

(b) Cell Extracts Preparation.

Cell extracts of *S. clavuligerus* cells were prepared from 1 liter (L) of *S. clavuligerus* growth culture. Cells were harvested by centrifugation (at 5,00×g for 5 min) at about 4° C., and washed twice with 0.2% KCl solution to remove traces of culture medium. Intracellular extracts were obtained by suspending washed cell pellets in 10 ml of water and heating them for 15 min at 100° C. The supernatant was separated by centrifugation at 15,000×g for 15 min and concentrated under reduced pressure to 1 ml.

(c) Separation of THP(A) from *S. clavuligerus* cell extracts.

Cell extract samples were mixed with 4 volumes of 1M acetic acid before separation by Dowex 50 W chromatography. The column was washed with deionized water (five times the column volume) to remove carbohydrates and polyols. Glutamate and THP(A) were eluted with 3M NH$_4$OH. Ammonia was evaporated to dryness and the residue was brought to pH 5 and separated by Dowex 1 anion exchange (acetate-form) chromatography. Glutamic acid remained attached to the anion exchange column while THP(A) was eluted with water.

(d) Crystallization of THP(A).

Pure THP(A) obtained above was dissolved in hot methanol and the solution was left in a desiccator under benzene vapor for crystallization. Crystals appeared after 7 days. The transparent, prismatic crystals having the dimensions 0.2× 0.1×0.05 mm were collected for X-ray structure analysis.

Example 9
Isolation and purification of THP(A) from cell extracts of *S. griseus*.

*Streptomyces griseus* (ATCC 10137) was grown in an agar medium (YM) containing: 1% malt extract, 0.4% yeast extract, 0.001% CaCl$_2$, 2% bacto-agar and 1 ml of trace salts stock solution per liter. The fermentation medium (FM) contained: 1.0% glycerol, 0.2% L-asparagine, 0.06% MgSO$_4$, 2.9% NaCl, 0.35% K$_2$HPO$_4$ and 0.68% KH$_2$PO$_4$ and 1 ml of trace salts stock solution per liter. Trace salts stock solution contained 100 mg FeSO$_4$×7H$_2$O, 100 mg MnCl$_2$×4H$_2$O, 100 mg ZnSO$_4$×4H$_2$O, and 100 mg CaCl$_2$ per 100 ml of water. The seed medium (SM) contained in addition to FM—0.1% of yeast extract and 0.1% NH$_4$Cl.

For the preparation of inoculum, strains were kept on YM agar plates at room temperature as a sporulating culture. Seed medium (200 ml in 1 liter Erlenmeyer flask) was inoculated by 1 ml spore suspension washed from the plate with 5 ml saline under aseptic conditions. Cells were cultivated at 30° C. and 210 rpm on a rotary shaker for 36 hours (final OD$_{540}$=3.6).

Fermentation. Cells from seed culture were harvested by centrifugation at 15000 g, washed with saline and cell pellet was homogenized in saline in a tissue homogenizer. Finally, the suspension served as an inoculum for 1 L FM medium in 5 L Erlenmeyer flask (OD$_{540}$=0.400). Cells were cultivated at 30° C. and 210 rpm on a rotary shaker for 38 hours (final OD$_{540}$=1.9). Mycellium was harvested by centrifugation and washed for following isolation of THP(A), carried out as in Example 8 above.

*S. griseus* can accumulate 1500 mg THP(A)/10L growth medium containing 0.5M NaCl, an amount much higher than that obtained with *S. clavuligerus* under similar conditions. The proton-decoupled $^{13}$C NMR spectrum of the extract of *S. griseus* grown in medium with 0.5M of NaCl for 66 hours is shown in FIG. 10, and of the produced THP(A) after purification is shown in FIG. 11.

REFERENCES

1. Brown, S. C., R. Mullis, C. Levenson, R. H. Shafer (1984) Biochemistry 23, 403.
2. Galinski, E. A., H. P. Pfeiffer and H. G. Truper (1985) Eur. J. Biochem. 149, 135.
3. Galinski, E. A. and K. Lippert (1991) in "General and Applied Aspects of Halophilic Microorganisms", F. Rodriquez-Valera (ed.), Plenum Press, New York. pp. 351–358.
4. Hodo and Blatti (1977) Biochem. 16, 2344.
5. Inbar, L. and A. Lapidot (1988a) J. Bacteriol. 170, 4055.
6. Inbar, L. and A. Lapidot (1988b) J. Biol. Chem. 263, 16014–16022.
7. Inbar, L. and A. Lapidot (1991) J. Bacteriol. 173, 7790.
8. Kadesch, T. R. and M. J. Chamberlin (1982) J. Biol. Chem. 257, 5286.
9. Lybrand et al. (1986) J. Mol. Biol. 191, 495–507.
10. Manley, J. L. (1984) in "Transcription and Translation A Practical Approach", B. D. Hames and S. J. Higgins (eds.), IRL Press, Washington D.C., p. 71.
11. Nosikov, V. V., E. A. Braga, A. Karlishev, A. L. Zhuse and O. L. Polyanovsky (1976) Nucl. Acids Res. 3, 2293–2301.
12. Nosikov, V. V. and B. Sain (1977) Nucl. Acids Res. 4, 2263–2273.
13. Peters, P., E. A. Galinski and H. G. Truper (1990) FEMS Microbiology Letters 71, 157–162.
14. Regev, R., I. Peri, H. Gilboa and Y. Avi-Dor (1990) Arch. Biochim. Biophys. 278, 106–112.
15. Schuh, W., H. Puff, E. A. Galinski, and H. G. Truper (1985) Z. Naturforsch. 40c, 780–784.
16. Wohlfarth, A., J. Severin and E. A. Galinski (1990) J. Gen. Microbiol. 136, 705–712.
17. Zhou, N., T. L. James and R. H. Shafer (1989) Biochemistry 28, 5231.

It is claimed:

1. A pharmaceutical composition comprising as active ingredient at least one tetrahydropyrimidine derivative selected from the group consisting of 2-methyl-4-carboxy-5-hydroxy-3,4,5,6-tetrahydropyrimidine [THP(A)], 2-methyl-4-carboxy-3,4,5,6-tetrahydropyrimidine [THP(B)] and pharmaceutically acceptable salts thereof, and a pharmaceutically acceptable carrier.

2. A pharmaceutical composition according to claim 1 comprising 2-methyl-4-carboxy-5-hydroxy-3,4,5,6-tetrahydropyrimidine [THP(A)].

3. A pharmaceutical compositions according to claim 1 comprising 2-methyl-4-carboxy-3,4,5,6-tetrahydropyrimidine [THP(B)].

4. A pharmaceutical composition according to claim 1 comprising THP(A) and THP(B).

5. A pharmaceutical composition according to claim 4 wherein THP(A) and THP(B) are present in equimolar amounts.

* * * * *